(12) United States Patent
Wang

(10) Patent No.: US 12,288,679 B2
(45) Date of Patent: Apr. 29, 2025

(54) METHOD FOR FULL Os ISOTOPE STATIC MEASUREMENT AT LOW-CONTENT/SMALL-SIZE SAMPLE

(71) Applicant: Guangzhou Institute of Geochemistry (GIG), Chinese Academy of Sciences (CAS), Guangdong (CN)

(72) Inventor: Guiqin Wang, Guangdong (CN)

(73) Assignees: Guangzhou Institute of Geochemistry (GIG), Guangdong (CN); Chinese Academy of Sciences (CAS), Guangdong (CN)

( * ) Notice: Subject to any disclaimer, the term of this patent is extended or adjusted under 35 U.S.C. 154(b) by 0 days.

(21) Appl. No.: 18/641,661

(22) Filed: Apr. 22, 2024

(65) Prior Publication Data

US 2024/0274423 A1 Aug. 15, 2024

(51) Int. Cl.
*H01J 49/00* (2006.01)
*H01J 49/04* (2006.01)
*H01J 49/16* (2006.01)

(52) U.S. Cl.
CPC ...... *H01J 49/0031* (2013.01); *H01J 49/0459* (2013.01); *H01J 49/16* (2013.01)

(58) Field of Classification Search
None
See application file for complete search history.

(56) References Cited

PUBLICATIONS

Yin, L. et al. Precise and accurate Re-Os isotope dating of organic-rich sedimentary rocks by thermal ionization mass spectrometry with an improved H2O2—HNO3 digestion procedure, International Journal of Mass Spectrometry, 421 (2017) 263-270 (Year: 2017).*
Liu, J. et al. Rapid, precise and accurate Os isotope ratio measurements of nanogram to sub-nanogram amounts using multiple Faraday collectors and amplifiers equipped with 1012 Q resistors by N-TIMS, Chemical Geology 363 (2014) 301-311 (Year: 2014).*
Chao Li, Xue Yang, Hong Zhao, Li-min Zhou, An-dao Du, Xin-wei Li, Wen-jun Qun. High Precise Isotopic Measurements of pg-ng Os by Negative Ion Thermal Ionization Mass Spectrometry[J]. Rock and Mineral Analysis, 2015, 34(4): 392-398. DOI: 10.15898/j.cnki.11-2131/td.2015.04.003.

(Continued)

*Primary Examiner* — Xiaoyun R Xu

(57) ABSTRACT

A method for full Os isotope static measurement by NTIMS includes steps of: selecting and weighing rock samples, and dissolving the rock samples to obtain dissolution liquid; chemically separating Os from the dissolution liquid to obtain purified Os solution; loading the purified Os solution on a Pt filament to obtain a sample to be determined; selecting Faraday cups and ion counters, as well as $10^{12}\Omega$ and $10^{13}\Omega$ amplifiers in NTIMS based on natural abundances of different Os isotopes, thereby establishing a cup configuration for the full Os isotope static measurement; establishing a yield calibration method for ICs; performing full Os isotopes static measurement based on the yield-calibrated ion counters and gain-calibrated faraday cups; and processing analytical data to obtain a final data of Os isotopic composition. The method enables the determination of the full Os isotope and oxygen isotope compositions of low-content or small-size samples.

18 Claims, 1 Drawing Sheet

(56) References Cited

PUBLICATIONS

Wang, G.Q. & Vollstaedt, Hauke & Xu, Jifeng & Liu, Wengui. (2019). High-Precision Measurement of 187Os/188Os Isotopic Ratios of Nanogram to Picogram Amounts of Os in Geological Samples by N-TIMS using Faraday Cups Equipped with 10$^{13}$ Ω Amplifiers. Geostandards and Geoanalytical Research. 43. 10.1111/ggr.12269.

Wang Wei, Chu Zhuyin, Li Chaofeng, Liu Wengui, Xu Junjie, Guo Jinghui, 2020. High-Precision Pb Isotope Ratio Determination of Zircon by Multi-Ion Counter TIMS with Multi-Dynamic Collection Method. Earth Science, 45(6):1977-1985. doi: 10.3799/dqkx.2019.285.

Wang G, Zeng Y, Xu J, Liu W. A new method for calibrating the current gain of 10$^{13}$ Ω amplifiers in thermal ionization mass spectrometry. J Mass Spectrom. Jun. 2018;53(6):455-464. doi: 10.1002/jms.4079. Epub Apr. 16, 2018. PMID: 29520915.

* cited by examiner

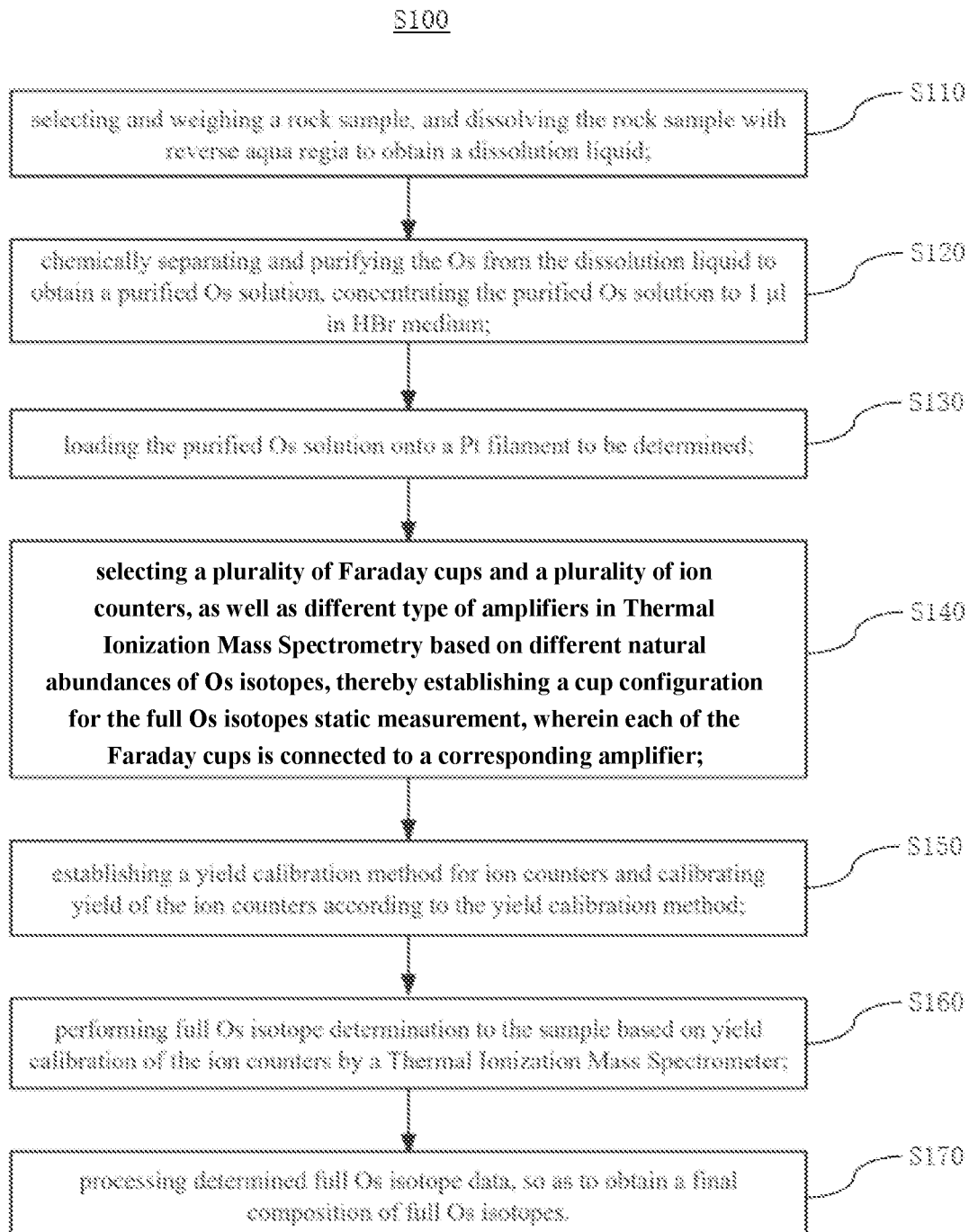

METHOD FOR FULL Os ISOTOPE STATIC MEASUREMENT AT LOW-CONTENT/SMALL-SIZE SAMPLE

CROSS REFERENCE OF RELATED APPLICATION

The present invention claims priority under 35 U.S.C. 119(a-d) to CN 202310562541.2, filed May 17, 2023.

BACKGROUND OF THE PRESENT INVENTION

Field of Invention

The present invention relates to a technical field of Os isotope tracing and dating, and more particularly to a method for full Os isotope static measurement at a low-content/small-size sample.

Description of Related Arts

In cosmochemical and geochemical studies, the three isotope ratios of Os, $^{184}Os/^{188}Os$, $^{186}Os/^{188}Os$, and $^{187}Os/^{188}Os$, are important due to their correlation with the three radioisotope systems $^{184}Os$-$^{180}W$, $^{190}Pt$-$^{186}Os$, and $^{187}Re$-$^{187}Os$, and the high-precision determination of these ratios is particularly important. Conventionally, the preferred instruments used for the high-precision determination of Os isotopes are Multi-Collector Inductively Coupled Plasma Mass Spectrometry (MC-ICPMS) and Thermal Ionization Mass Spectrometry (TIMS), both of which are based on the same principle of measurement, but with different injection forms. The MC-ICPMS adopts liquid injection, and the TIMS adopts solid injection. TIMS is more widely used because of the absence of memory effect and the advantage that the main interfering element Re, which remains due to incomplete purification, can be effectively removed during the heating process of sample determination. In order to improve the ionization efficiency, the Os isotopes were measured using the negative ion mode Thermal Ionization Mass Spectrometry (NTIMS) for the $OsO_3^-$ ion beam. Accurate Os isotopic compositions require deoxygenation calculations. Therefore, the accuracy of oxygen isotope composition directly affects the precision and accuracy of Os isotopes.

Conventionally, the commonly adopted method for Os isotope determination is negative ion mode Thermal Ionization Mass Spectrometry (NTIMS), in which Os isotopes, isobaric interferences, and oxygen isotopes are collected by Faraday Cups connected to conventional $10^{11}\Omega$ amplifiers. This scheme can only realize the static high-precision determination of large size samples (the total amount of Os is greater than 4 ng, and the corresponding rock samples need to be several grams to tens of grams, or even more). For small size sample, the signals of $^{184}Os$ may be below the detection limit of the instrument and cannot be recognized (the natural abundance of $^{184}Os$ is only 0.02%), and the precision of the determination of $^{186}Os$ and $^{187}Os$ will also be worse. In addition, the conventional NTIMS method is limited by the instrumental hardware, which cannot determine all seven Os isotopes while obtaining data for all three oxygen isotopes and other interfering elements. The conventional method of MC-ICPMS also can only realize the static high-precision determination of large size samples, and the instrument has a strong memory effect on Os, which could cause a significant deteriorate in the accuracy when multiple samples are measured consecutively.

None of the conventional Os isotope determination methods can realize the static measurement of all seven isotopes of Os, isobaric interferences and all three oxygen isotopes. The conventional method can only analyze the $^{186}Os/^{188}Os$ and $^{187}Os/^{188}Os$ isotope ratios or one of them for a small size sample, and cannot realize the static measurement of the three oxygen isotopes at the same time. In conclusion, there is no high-precision Os isotope measurement method that can realize the static determination of all Os isotopes and oxygen isotope compositions for samples with small-size or low-content Os.

SUMMARY OF THE PRESENT INVENTION

An object of the present invention is to provide a method for full Os isotope static measurement at a low-content/small-size sample, so as to solve at least one of the technical problems in the prior art.

Accordingly, the present invention provides a method for full Os isotope static measurement at a low-content/small-size sample, comprising steps of:

selecting and weighing a rock sample, and dissolving the rock sample with reverse aqua regia to obtain a dissolution liquid;

chemically separating and purifying the Os from the dissolution liquid to obtain a purified Os solution, concentrating the purified Os solution to 1 µl in HBr medium;

loading the purified Os solution onto a high purity Pt filament to be determined;

selecting a plurality of Faraday cups and a plurality of ion counters, as well as different types of amplifiers in Thermal Ionization Mass Spectrometry based on different natural abundances of Os isotopes, thereby establishing a cup configuration for the full Os isotope static measurement, wherein each Faraday cup is connected to a corresponding different type of amplifier;

establishing a yield calibration method for the ion counters and calibrating yield of the ion counters according to the yield calibration method;

performing full Os isotope determination to the sample based on yield calibration of the ion counters by Thermal Ionization Mass Spectrometry; and processing determined full Os isotope data, so as to obtain a final composition of full Os isotopes.

Preferably, the plurality of the Faraday cups comprises a center cup (C) fixed to a multicollector housing of the Thermal Ionization Mass Spectrometry, a first low cup (L1), a second low cup (L2), a third low cup (L3), a fourth low cup (L4), a fifth low cup (L5), a first high cup (H1), a second high cup (H2), a third high cup (H3), and a fourth high cup (H4) disposed sequentially outwardly from the center cup; the plurality of the ion counters comprises a first ion counter (IC 1) bound to the center cup, a second ion counter (IC 2) and a third ion counter (IC 3) and a fourth ion counter (IC4) bound in turn to the fifth low cup (L5), and a fifth ion counter (IC5) and a sixth ion counter (IC6) bound in turn to the fourth low cup (L4);

the cup configuration for the full Os isotope static measurement comprises:

$^{188}OsO_3^-$, $^{189}OsO_3^-$, $^{190}OsO_3^-$ and $^{192}Os^{16}O_3^-$ are collected by the second low cup (L2), the first low cup (L1), the center cup (C) and the first high cup (H1) connected with four $10^{12}\Omega$ amplifiers, respectively;

$^{186}OsO_3^-$ and $^{187}OsO_3^-$ are collected by the fourth low cup (L4) and the third low cup (L3) connected with two $10^{13}\Omega$ amplifiers, respectively;

$^{184}OsO_3^-$ is collected by the sixth ion counter (IC6);

$^{195}PtO_3^-$ is collected by the fourth high cup (H4) connected with on $10^{13}\Omega$ amplifier;

$^{198}PtO_2^-$ is collected by the fifth ion counter (IC5);

a heavy oxygen ion beam $^{192}Os^{16}O_2^{17}O^-$ is collected by the second high cup (H2) connected with one $10^{13}\Omega$ amplifier; and a heavy oxygen ion beam $^{192}Os^{16}O_2^{18}O^-$ is collected by the third high cup (H3) connected to a $10^{13}\Omega$ amplifier.

Preferably, the fifth ion counter (IC5) and the sixth ion counter (IC6) are both compact discrete dynode ion counters.

Preferably, establishing the yield calibration method for the ion counters (ICs) and calibrating the yield of the ion counters according to the yield calibration method comprises a specific step of:

determining the $^{192}Os^{16}O_3^-$ using the center cup (C) and the ion counters (ICs), respectively, in a peak-hopping manner, wherein the center cup (C) is used to determine the $^{192}Os^{16}O_3^-$ both before and after determining the $^{192}Os^{16}O_3^-$ by the ion counters (ICs);

a yield $Y_N$ of the ion counters (ICs) is expressed as:

$$Y_N = (A + D)/2/B \times 100\%;$$

wherein A is a signal of a first $^{192}Os^{16}O_3^-$ determination using the center cup (C), B is a signal of a $^{192}Os^{16}O_3^-$ determination using the ion counters (ICs), and D is a signal of a second $^{192}Os^{16}O_3^-$ determination using the center cup (C).

Preferably, selecting and weighing the rock sample, and dissolving the rock sample to obtain the dissolution liquid comprises specific steps of:

selecting at least 3 rock samples to be determined and weighing 0.5-1.0 g of each rock sample; and putting the rock samples into a Carius tube (a glass tube), adding 1 ml-3 ml of concentrated HCl and 3 ml-9 ml of concentrated $HNO_3$ to the glass tube, wherein a ratio of $HCl:HNO_3$ is 1:3, sealing the Carius tube, and dissolving the rock samples in an oven at 200° C.-250° C. for 48 hr-72 hr, so as to obtain the dissolution liquid.

Preferably, chemically separating the Os from the dissolution liquid to obtain the purified Os solution comprises specific steps of:

distilling the dissolution liquid for extracting the Os; and purifying extracted Os by micro-distillation to obtain a further purified Os solution.

Preferably, loading the purified Os solution to a filament to be determined comprises specific steps of:

concentrating the purified Os solution in HBr medium to 1 µl-2 µl, loading the purified Os solution onto a high-purity Pt filament and drying at 0.5 A current;

loading 1 µl~2 µl of $Ba(OH)_2$ at a concentration of 10 ppm-20 ppm on dried sample as an activitor, and drying at 0.5 A current to obtain the sample to be determined.

Preferably, performing full Os isotope determination to the sample based on the yield calibration of the ion counters by the Thermal Ionization Mass Spectrometry comprises specific steps of:

during measurement, maintaining an oxygen pressure at $1.5 \times 10^{-7}$ mbar-$2.5 \times 10^{-7}$ mbar and analyzing for 1 hr-1.5 hr per each time, wherein an evaporation filament temperature is 700° C.-830° C. for Os single-element standard measurement, and an evaporation filament temperature is 830° C.-890° C. for rock sample measurement; and before and after each sample measurement, determining $^{185}ReO_3$ and $^{183}WO_3$ using an SEM (secondary electron multiplier) by peak-hopping method to monitor isobaric interferences of Re and W;

wherein a peak-hopping analytical parameter ranges from 8 cycles×1 block to 12 cycles×1 block, an integration time ranges from 2 s-4 s, and a time period of one measurement ranges from 1 min-2 min.

Preferably, processing the determined full Os isotope data, so as to obtain the final composition of the full Os isotopes comprises a specific step of:

exporting the determined data for offline correction processing; wherein the offline correction processing comprises removing the isobaric interferences of $PtO_2$, $PtO_3$, $ReO_3$ and $WO_3$, subtracting interferences of heavy O isotopes in oxides, and performing an instrumental mass fractionation correction by a logarithmic law using $^{192}Os/^{188}Os=3.083$.

Preferably, before performing full Os isotope determination to the sample based on the yield calibration of the ion counters by the Thermal Ionization Mass Spectrometry, the method further comprises a step of:

automatically calibrating the amplifier gain according to an automatic calibration method for the Thermal Ionization Mass Spectrometry.

The present invention provides a method for full Os isotope static determination at a low-content/small-size sample, thus selecting a plurality of Faraday cups and a plurality of ion counters, as well as different types of amplifiers for a Thermal Ionization Mass Spectrometry based on natural abundances of 7 Os isotopes, thereby establishing a cup configuration for the full Os isotope static measurement; and performing full Os isotope determination of the sample to be determined based on the established cup configuration. The method of the present invention adopts a combination of different types of collectors (FC, CDD) and different types of amplifiers ($10^{12}\Omega$ and $10^{13}\Omega$) to solve the problem of extremely differences in abundance among Os isotopes and the problem that the number of isotopes to be determined is more than the maximum limiting number of Faraday cups in the instrument, which ensures that both the high signals and the low signals are higher than the detection limits of the detectors, and can be accurately determined.

The method of the present invention uses $10^{12}\Omega$ and $10^{13}\Omega$ amplifiers to replace the conventional $10^{11}\Omega$ amplifiers, so as to realize high-precision Os isotope determination of a small-size sample or a low-content (the total amount of Os is less than 4 nanograms) sample. When the sample size is only ⅕-1/10 of the conventional Os amount, it is possible to obtain the best precision compared with that of conventional methods. The method is especially adapted to the determination of precious samples, for example, Moon, Mars and other precious samples.

The method of the present invention realizes the simultaneous static determination of 11 isotopes. While obtaining the full isotopic composition of Os and O, and Pt oxide data can also be obtained. The isotope ratios of $^{184}Os/^{188}Os$, $^{186}Os/^{188}Os$ and $^{87}Os/^{188}Os$ can be obtained by one measurement, which greatly improves efficiency and reduces research cost and time.

The method of the present invention establishes a yield calibration method for ion counters (ICs), calibrates yield of ion counters (ICs) according to the yield calibration method, and performs a full Os isotope static measurement according to the yield-calibration ion counters, which improves the accuracy and precision of the full Os isotope static determination, making the results more reliable.

BRIEF DESCRIPTION OF THE DRAWINGS

FIGURE is a flow chart of a method for isotope static determination of full Os at a low-content/small-size sample according to a preferred embodiment of the present invention.

DETAILED DESCRIPTION OF THE PREFERRED EMBODIMENT

In order to enable a person skilled in the art to better understand the technical solutions of the present invention, the present invention will be further described below in conjunction with the accompanying drawing and embodiment.

The high-precision and high-accuracy determination of Os isotopes requires three conditions: 1. accurate determination of all Os isotopes (a total of 7); 2. accurate determination of isobaric interferences of Os isotopes (e.g., $^{187}ReO_3$ interference with $^{187}OsO_3$; $^{186}WO_3$ interference with $^{186}OsO_3$); and 3. accurate determination of oxygen isotopic composition. In order to realize high-precision and high-accuracy determination of Os isotopes, the present invention provides a method for full Os isotope static measurement on a low-content/small-size sample.

Referring to FIGURE, a method S100 for full Os isotopes static measurement on a low-content/small-size sample is illustrated, comprising steps as follows.

S110: selecting and weighing a rock sample, and dissolving the rock sample with reverse aqua regia to obtain a dissolution liquid.

First, selecting at least 3 rock samples to be determined and weighing 0.5-1.0 g of each rock sample.

Specifically, according to the embodiment, three rock samples, WPR-1 (metamorphic peridotite), BIR-1a (basalt), and BHVO-2 (basalt), were selected for the experiment. These three rock samples are also international geological reference materials that represent typical mantle lithologies and cover the Os content range of most mantle rocks (13300 pg/g, 350 pg/g, and 76 pg/g, respectively). About 0.9 g of each sample was weighed during this experiment, and the theoretically calculated maximum values of amount Os used for the determination of the three samples were 12 ng, 306 pg, and 66 pg, respectively.

Then, putting the rock samples to be determined into a Carius tube (a glass tube), adding 1 ml-3 ml of concentrated HCl and 3 ml-9 ml of concentrated $HNO_3$ to the glass tube, wherein a ratio of $HCl:HNO_3$ is 1:3, sealing the Carius tube, and dissolving the rock samples in an oven at 200° C.-250° C. for 48 hr-72 hr, so as to obtain the dissolution liquid.

Specifically, according to the embodiment, the three weighed rock samples WPR-1 (metamorphic peridotite), BIR-1a (basalt) and BHVO-2 (basalt) were put into glass tubes, 2 ml of concentrated HCl and 6 ml of concentrated $HNO_3$ (reverse aqua regia, the temperature of $HNO_3$ was −18° C. to avoid the loss of Os caused by its addition; If a concentration measurement of Os is required, a spike should be added before the reverse aqua regia). The tubes were then sealed, and the samples were dissolved for 48 hrs in an oven at 240° C., to get the dissolution liquid.

S120: chemically separating the Os from the dissolution liquid to obtain a purified Os solution.

First, distilling the dissolution liquid for extracting the Os.

Specifically, according to the embodiment, the dissolved samples were taken out for extracting the Os by distilling.

Then, purifying extracted Os by micro-distillation to obtain the more finely purified Os solution.

Specifically, according to the embodiment, after the Os was extracted by distilling, the extracted Os was then purified again by micro-distillation to obtain the purified Os solution.

S130: loading the purified Os solution on a high purity Pt filament to obtain a sample to be determined.

Specifically, evaporating the purified Os solution in HBr medium to a residue of 1 µl-2 µl, loading the purified Os solution onto a high-purity Pt filament and drying; loading 1 µl~2 µl of $Ba(OH)_2$ at a concentration of 10 ppm-20 ppm as an activator, and drying again to obtain the sample to be determined.

According to the embodiment, the purified Os solution was distilled to 1 µl-2 µl in HBr medium, then loaded onto a high-purity Pt filament and dried again; a further 1 µl of $Ba(OH)_2$ at a concentration of 15 ppm was loaded as an activator and then drying again to obtain the sample to be determined. After the sample loading, the Pt filament was loaded onto the sample wheel, and then placed it into sample house of the Thermal Ionization Mass Spectrometry for analysis. In other words, after this step, various treatments of the sample to be measured are completed.

S140: selecting a plurality of Faraday cups (FCs) and a plurality of ion counters (ICs), as well as different types of amplifiers in Thermal Ionization Mass Spectrometry based on natural abundances of different Os isotopes, thereby establishing a cup configuration for the full Os isotopes static measurement, wherein each of the Faraday cups is connected to a corresponding different type of amplifier.

Specifically, this method is based on the Thermal Ionization Mass Spectrometry instrument from Thermo Fisher Scientific, which is currently the most widely used instrument in the world. This Thermal Ionization Mass Spectrometry equipped with Faraday cups, ion counters (ICs), and three types of amplifiers: $10^{11}\Omega$, $10^{12}\Omega$, and $10^{13}\Omega$. The new type Thermal Ionisation Mass Spectrometry can be configured with instrument hardware suitable for Os measurement of low-content/small-size samples. Specifics include the maximum number of Faraday cups that can be reached (FC, 10), the optimal configuration of amplifiers (10 amplifiers: one $10^{11}\Omega$, four $10^{12}\Omega$, five $10^{13}\Omega$), and six ion counters (ICs), wherein each of the Faraday cups can be connected to any of the amplifiers. The ion counters consist of 3 secondary electron multipliers (SEM, abbreviated as IC1, IC2, and IC3) and 3 compact discrete dynodes (CDD, abbreviated as IC4, IC5, and IC6). More specifically, in this embodiment, according to the natural abundance of the 7 Os isotopes, as shown in Table 1, corresponds to a plurality of Faraday cups in the Thermal Ionization Mass Spectrometry, comprising a fixed center cup C in the multi-collector housing, 5 low cups sequentially set outwardly from the central cup C, namely, a first low cup L1, a second low cup L2, a third low cup L3, a fourth low cup L4, a fifth low cup L5, respectively. 4 high cups are also provided, that is, a first high cup H1, a second high cup H2, a third high cup H3, and a fourth high cup H4 sequentially set outwardly from the central cup C. That is to say, on one side of the center cup C were five low cups set outwards in sequence, and on the other side of the center cup C were four high cups set outwards in sequence. Among them, the positions of the center cup C and the fifth low cup L5 were fixed and immovable, and all other Faraday cups could be differently placed according to different isotope determination requirements. In this case, each Faraday cup was connected to an amplifier of matching type according to the natural abundance of Os isotope. The plurality of the ion counters comprises a first ion counter IC1 bound to the center cup C, a second ion counter IC2 and a third ion counter IC3 and a fourth ion counter IC4 sequentially bound to the fifth low cup L5, and a fifth ion counter IC5 and a sixth ion counter IC6 sequentially bound to the fourth low cup L4. The first ion counter IC1, the second ion counter IC2, and the third ion counter IC3 employed a secondary electron multiplier (SEM), and the fourth ion counter IC4, the fifth ion counter IC5, and the sixth ion counter IC6 employed a compact discrete dynode (CDD) ion counter.

It should be noted that based on the natural abundance of the 7 Os isotopes, the interfering element isotopes, and the oxygen isotope abundance characteristics, as shown in Table 1, cup configuration established according to the embodiment adopted two compact discrete dynode (CDD) ion counters for Os isotopes, namely the fifth ion counter IC5 and the sixth ion counter IC6, wherein the fifth ion counter IC5 and the sixth ion counter IC6 were bound to the fourth lower cup L4.

Based on the natural abundance of the 7 Os isotopes, the embodiment adopts $10^{12}\Omega$ and $10^{13}\Omega$ amplifiers to replace the conventional $10^{11}\Omega$ amplifiers, so as to realize high-precision Os isotope determination of a small-size or a low-content sample (the total amount of Os is less than 4 nanograms). Since the signal-to-noise ratios of the $10^{12}\Omega$ and $10^{13}\Omega$ amplifiers are 3 and 10 times higher than those of the conventional $10^{11}\Omega$ amplifiers, the two amplifiers can theoretically be used to obtain results that are consistent with the optimum precision of the conventional method when the sample size is 1/3-1/10 of the conventional sample size.

The method according to the embodiment of the present invention uses $10^{12}\Omega$ and $10^{13}\Omega$ amplifiers to replace the conventional $10^{11}\Omega$ amplifiers, so as to realize high-precision Os isotope determination of a small-size or a low-content sample (the total amount of Os is less than 4 nanograms). When the sample size is only 1/5-1/10 of the conventional amount, it is possible to obtain the higher precision compared with that of conventional methods. The method is especially adapted to the determination of precious samples of, for example, Moon and Mars, and other precious samples.

According to the embodiment, a combination of different types of collectors (FC, CDD) and different types of amplifiers ($10^{12}\Omega$ and $10^{13}\Omega$) are used to solve the problem of the extremely differences in abundance between Os isotopes (e.g., there is a more than 2,000-fold difference between the largest natural abundance of $^{192}$Os and the smallest natural abundance of $^{184}$Os) as well as the problem that the number of isotopes to be determined exceeds the maximum limit number of Faraday cups for which the instrument can be configured.

Exemplarily, the cup configuration for the full isotope static determination of the Os is as follows.

Referring to Table 1, based on the natural abundance of the 7 Os isotopes, four ion beams with high abundances, $^{188}$OsO$_3^-$, $^{189}$OsO$_3^-$, $^{19}$OsO$_3^-$ and $^{192}$Os$^{16}$OsO$_3^-$, are collected by the second low cup L2, the first low cup L1, the center cup C and the first high cup H1 connected with $10^{12}\Omega$ amplifiers, respectively.

It should be noted that if $^{190}$Os spike is added and the signal is too high, the center cup C, which collects $^{190}$OsO$_3^-$, can be connected with a $10^{11}\Omega$ amplifier.

Referring to Table 1, two ion beams with low abundances, $^{186}$OsO$_3^-$ and $^{187}$OsO$_3^-$, are collected by the fourth low cup L4 and the third low cup L3 connected to two $10^{13}\Omega$ amplifiers, respectively.

Referring to Table 1, one ion beam with extremely low abundance, $^{184}$OsO$_3^-$, is collected by the sixth ion counter IC6. That is to say, ion beam $^{184}$OsO$_3^-$ with extremely low abundance is collected by the CDD of the sixth ion counter IC6.

$^{195}$PtO$_3^-$ and $^{198}$PtO$_2^-$ are used to monitor the interferences of trioxides and dioxides of Pt, respectively. As shown in Table 1, the cup configuration established is also capable of determining the dioxides and trioxides of elemental platinum simultaneously.

Specifically, as shown in Table 1, $^{195}$PtO$_3^-$ is collected by the fourth high cup H4 connected to $10^{13}\Omega$ amplifier; and $^{198}$PtO$_2^-$ is collected by the fifth ion counter IC5. That is to say, $^{198}$PtO$_2^-$ is collected by the CDD of fifth ion counter IC5.

In addition, the oxygen isotope composition can be obtained by determining $^{192}$Os$^{16}$O$_3$ (atomic mass 240) and the oxide molecules $^{192}$Os$^{16}$O$_2^{17}$O (atomic mass 241) and $^{192}$Os$^{16}$O$_2^{18}$O (atomic mass 242) containing the heavy oxygen isotopes ($^{17}$O and $^{18}$O). As shown in Table 1, all three isotopes of oxygen can be determined simultaneously by the established cup configuration.

Specifically, as shown in Table 1, a heavy oxygen ion beam $^{192}$Os$^{16}$O$_2^{17}$O is collected by the second high cup H2 connected to a $10^{13}\Omega$ amplifier.

A heavy oxygen ion beam $^{192}$Os$^{16}$O$_2^{18}$O is collected by the third high cup H3 connected to a $10^{13}\Omega$ amplifier.

The method according to the embodiment of the present invention selects a plurality of Faraday cups and a plurality of ion counters (ICs), as well as different type of amplifiers in Thermal Ionization Mass Spectrometry based on different natural abundances of Os isotopes, thereby establishing a cup configuration for the full Os isotope static measurement. The method realizes the simultaneous static determination of 11 isotopes. While obtaining the full Os isotopic composition, O isotopic composition and Pt oxide data can also be obtained. The isotope ratios of $^{184}$Os/$^{188}$Os, $^{186}$Os/$^{188}$Os and $^{87}$Os/$^{188}$Os can be obtained by one measurement, which greatly improves efficiency and reduces research cost and time.

It should be noted that the largest beam size collected by Faraday cups with $10^{12}\Omega$ amplifiers should be lower than 1.2 V in the negative mode. In the embodiment, none of the samples is added spike. Based on $^{192}$Os with the largest natural abundance, when intensity of the $^{192}$Os$^{16}$O$_3^-$ ion beam is 1.2 V, intensities of the $^{186}$OsO$_3^-$ and $^{187}$O$_3^-$ ion beam are then below 60 mV, and intensity of the $^{184}$Os O$_3^-$ ion beam is below 0.6 mV.

It should be further noted that $^{185}$ReO$_3$ and $^{183}$WO$_3$ were measured. Based on the natural abundance ratios of $^{187}$Re/$^{185}$Re=1.67, $^{184}$W/$^{183}$W=2.14, and $^{186}$W/$^{183}$W=1.99, the isobaric interference of $^{187}$ReO$_3$, $^{184}$WO$_3$ and $^{186}$WO$_3$ on $^{187}$OsO$_3$, $^{184}$OsO$_3$, and $^{186}$OsO$_3$ were subtracted. $^{185}$ReO$_3$ and $^{183}$WO$_3$ were determined by SEM peak-hopping method for about 1.5 min before and after each sample measurement (10 cycles×4 s integration time×1 block).

TABLE 1 cup configuration for full Os isotope static measurement

| Collector | IC5 | IC6 | L4 | L3 | L2 | L1 | C | H1 | H2 | H3 | H4 |
|---|---|---|---|---|---|---|---|---|---|---|---|
| Type (IC/Amp.) | CDD | CDD | $10^{13}$ Ω | $10^{13}$ Ω | $10^{12}$ Ω | $10^{12}$ Ω | $10^{12}$ Ω | $10^{12}$ Ω | $10^{13}$ Ω | $10^{13}$ Ω | $10^{13}$ Ω |
| Atomic mass | 230 | 232 | 234 | 235 | 236 | 237 | 238 | 240 | 241 | 242 | 243 |
| Ion beam | $^{198}PtO_2^-$ | $^{184}OsO_3^-$ | $^{186}OsO_3^-$ | $^{187}OsO_3^-$ | $^{188}OsO_3^-$ | $^{189}OsO_3^-$ | $^{190}OsO_3^-$ | $^{192}Os^{16}O_3^-$ | $^{192}Os^{16}O_2^{17}O$ | $^{192}Os^{16}O_2^{18}O$ | $^{195}PtO_3^-$ |
| Natural abundance | | 0.02 | 1.59 | 1.96 | 13.24 | 16.15 | 26.26 | 40.78 | | | — |

Note:
IC—ion counter;
Amp.—amplifier.

S150: establishing a yield calibration method for ICs and calibrating the yield of ion counters according to the yield calibration method.

The yield calibration of ion counters is critical to the precision and accuracy of the measurements. The instrument supplier, Thermo Fisher Scientific only provides an automatic yield calibration procedure for the first ion counter IC1 (SEM bounded to the Faraday cup of center cup C), and not for any of the other ion counters. Therefore, although many instruments are configured with more than one ion counter, their applications are greatly limited. In the embodiment, two CDD ion counters were used, namely the fifth ion counter IC5 and the sixth ion counter IC6 for collecting ion beams $^{198}PtO_2^-$ and $^{184}OsO_3^-$ with atomic mass of 230 and 232, respectively. In order to accurately determine them, we established a yield calibration method for the ion counters (IC), i.e., we established a yield calibration method for the CDD ion counters to solve the problem that the supplier did not provide an automatic calibration procedure for the other ion counters.

Exemplarily, establishing the yield calibration method for ion counters (ICs) and calibrating the yield of ion counters according to the yield calibration method comprises a specific step of:

determining a stable signal $^{192}Os^{16}O_3^-$ using the center cup C and the ion counters (IC5 and IC6) by peak-hopping, wherein the center cup C is used to determine the $^{192}Os^{16}O_3^-$ both before and after determining the $^{192}Os^{16}O_3^-$ by the ion counters;

a yield $Y_N$ of the ion counters is expressed as:

$$Y_N = (A + D)/2/B \times 100\%;$$

wherein A is a signal of a first $^{192}Os^{16}O_3^-$ determination using the center cup C, B is a signal of a $^{192}Os^{16}O_3^-$ determination using the ion counters, and D is a signal of a second $^{192}Os^{16}O_3^-$ determination using the center cup C.

Specifically, according to the embodiment, $^{192}Os^{16}O_3^-$ (signal intensity of about 2.5 mV, or 150,000 cps) was measured by peak-hopping using the center cup C of the Faraday cups, the fifth ion counter IC5 and the sixth ion counter IC6. The center cup C can be connected to a $10^{11}$ Ω, $10^{12}$ Ω or $10^{13}$ Ω amplifier, and was done gain-calibration before measurement. The signal measured by C with a $10^{12}$ Ω amplifier was used as a benchmark, and the signal measured in turn by IC5 and IC6 was evaluated as the target. The intensity of the ion beam measured by the Faraday cup was expressed in volts (V), and the intensity of the ion beam measured by the CDD ion counter was expressed in counts per second (cps). A conversion factor between cps and V is 6250 cps $fA^{-1}$ (i.e., 62,500 cps $mV^{-1}$).

TABLE 2

Measurement and calculation methods for IC5 and IC6 yield calibration

| Order | Collector | IC5 | IC6 | C/SEM | Signal (V) | $Y_N$ (%) |
|---|---|---|---|---|---|---|
| 1 | 240inC | | | $^{192}OsO_3$ | a | |
| 2 | 240inIC5 | $^{192}OsO_3$ | | | 248.42 b | $Y_{IC5} = (a + c)/2/ b \times 100\%$ |
| 3 | 240inC | | | $^{192}OsO_3$ | c | |
| 4 | 240inIC6 | | $^{192}OsO_3$ | | 246.36 d | $Y_{IC6} = (c + e)/2/ d \times 100\%$ |
| 5 | 240inC | | | $^{192}OsO_3$ | e | |

The established yield calibration method for ICs and the procedure for yield calibration of the ion counters are shown in Table 2. The order of determination of the center cup C is 1, 3, and 5; the order of determination of the fifth ion counter IC5 and the sixth ion counter IC6 is 2 and 4. That is to say, before and after the determination of each signal by the ion counters (IC5 and IC6), the center cup C is used for determination. The yield is then calculated from the measurement results of the two type collectors, wherein the average of the measured values of the center cup C before and after each ion counter (IC5 and IC6) measurement is used as the benchmark for the calculation, so as to eliminate small variations in signals over time. The amplifier connected to the center cup C can be a $10^{11}$ Ω, $10^{12}$ Ω or $10^{13}$ Ω amplifier, depending on the signal intensity, and the ion beam is required to be stable at all times during the measurement.

Referring to Table 2, the center cup C is used for the measurement of $^{192}Os^{16}O_3^-$, and the detected signal of $^{192}Os^{16}O_3^-$ is a; then the fifth ion counter IC5 is used for the measurement of $^{192}Os^{16}O_3^-$, and the detected signal of $^{192}Os^{16}O_3^-$ is b; and the center cup C is used again for the measurement of $^{192}Os^{16}O_3^-$, and the detected signal of $^{192}Os^{16}O_3^-$ is c. As a result, the yield of the fifth ion counter IC5, $Y_{IC5}=(a+c)/2/b\times 100\%$.

Referring to Table 2, the center cup C is used for the measurement of $^{192}Os^{16}O_3^-$, and the detected signal of $^{192}Os^{16}O_3^-$ is c; then the sixth ion counter IC6 is used for the measurement of $^{192}Os^{16}O_3^-$, and the detected signal of $^{192}Os^{16}O_3^-$ is d; and the center cup C is used again for the measurement of $^{192}Os^{16}O_3^-$, and the detected signal of $^{192}Os^{16}O_3^-$ is e. As a result, the yield of the sixth ion counter IC6, $Y_{IC6}=(c+e)/2/d\times 100\%$.

Exemplarily, before performing full Os isotope determination to the sample based on the yield calibration of the ion counters by the Thermal Ionization Mass Spectrometry, the method further comprises a step of:

automatically calibrating the gain of amplifiers using an automatic calibration method provided by the supplier of the Thermal Ionization Mass Spectrometry. Specifically, in the embodiment, the amplifiers are gain-calibration using an automatic gain calibration method, wherein the amplifiers ($10^{11}$ Ω, $10^{12}$Ω, and $10^{13}$Ω) are done gain-calibration once a week with a virtual current of 0.12 V.

The method according to the embodiment of the present invention establishes a yield calibration method for ICs, calibrates a yield of ion counters according to the yield calibration method, and performs a full Os isotope static measurement according to the yield-calibrated ion counters and gain-calibrated amplifiers connected to the Faraday cups, which improves the accuracy and precision of the full Os isotope static measurement, making the results more reliable.

S160: performing full Os isotope determination to the sample based on yield calibration of the ion counters by the Thermal Ionization Mass Spectrometry.

According to the embodiment, performing full Os isotope determination of the sample using Thermal Ionization Mass Spectrometry based on the yield-calibrated CDD ion counters comprises specific steps of:

during measurement, maintaining an oxygen pressure at $1.5\times 10^{-7}$ mbar-$2.5\times 10^{-7}$ mbar and measuring for 1 hr-1.5 hr per each time, wherein an evaporation filament temperature is 700° C.-830° C. for solution standard measurement, and an evaporation filament temperature is 830° C.-890° C. for rock sample measurement; and before and after each sample measurement, determining $^{185}ReO_3$ and $^{183}WO_3$ by SEM (secondary electron multiplier) peak-hopping method to monitor isobaric interferences of Re and W; wherein a peak-hopping determination analytical parameter ranges from 8 cycles×1 block to 12 cycles×1 block, an integration time ranges from 2 s-4 s, and a time period of a single determination ranges from 1 min-2 min.

Specifically, according to the embodiment, Os and interfering elements were measured as trioxide ions in the negative mode. The baseline of the instrument was measured once a day before the start analysis work, with a pre-wait of 60 s, and 1200 cycles×integration time 1.05 s. The automatic gain calibration of the amplifiers ($10^{11}$ Ω, $10^{12}$Ω, and $10^{13}$Ω) was performed once a week, with a virtual current of 0.12 V. Each sample was measured 20 cycles×10 blocks (i.e., 200 data), with an integration time of 16 s, and an idle time of 12 s. During the measurements, the oxygen pressure was maintained at $1.5\times 10^{-7}$ mbar-$2.5\times 10^{-7}$ mbar, regulated by a needle valve. Each measurement took about 1.1 hr. The evaporation filament temperature was 700° C.-830° C. for solution standard measurements and 830° C.-890° C. for rock sample measurements. Atomic masses 233 and 231 (i.e., $^{185}ReO_3$ and $^{183}WO_3$) were measured with the SEM peak-hopping method before and after each sample determination to monitor isobaric interferences of Re and W. The mass numbers were determined using the SEM peak-hopping method. The peak-hopping analytical parameter was 10 cycles×1 block, the integration time was 4 s, and the time period for one measurement was about 1.2 min.

Referring to Table 3, the method according to the embodiment of the present invention realizes the simultaneous static determination of 11 isotopes, including the full Os isotopic composition, O isotopic composition and Pt oxide data. The isotope ratios of $^{184}Os/^{188}Os$, $^{186}Os/^{188}Os$ and $^{87}Os/^{188}Os$ can be obtained by one measurement, which greatly improves efficiency and reduces research cost and time.

TABLE 3

| | full Os isotope measurements on a real sample | | | | | | | | | | |
|---|---|---|---|---|---|---|---|---|---|---|---|
| Ion beam | $^{186}Os$ $O_3$ | $^{187}Os$ $O_3$ | $^{188}Os$ $O_3$ | $^{189}Os$ $O_3$ | $^{190}Os$ $O_3$ | $^{192}Os$ $O_3$ | $^{192}Os^{16}O_2$ $^{17}O$ | $^{192}Os^{16}O_2$ $^{18}O$ | $^{195}Pt$ $O_3$ | $^{198}Pt$ $O_2$ | $^{184}Os$ $O_3$ |
| Collector | L4 | L3 | L2 | L1 | C | H1 | H2 | H3 | H4 | IC5 | IC6 |
| Intensity | 0.02 | 0.017 | 0.16 | 0.20 | 0.33 | 0.51 | 0.00058 | 0.0030 | 8.5E−09 | 1086 | 13362 |
| Unit | V | V | V | V | V | V | V | V | V | cps | cps |

S170: processing determined full Os isotope data, so as to obtain a final composition of full Os isotopes.

Exemplarily, processing the determined full Os isotope data comprises a specific step of:

specifically, exporting the determined data for offline correction processing; wherein the offline correction processing comprises subtracting isobaric interferences of $PtO_2$, $PtO_3$, $ReO_3$ and $WO_3$, subtracting interferences of O isotopes, and performing a mass fractionation correction by a logarithmic law using $^{192}Os/^{188}Os=3.083$.

TABLE 4

Os isotope ratios of standard solutions and rock samples were obtained by full Os isotope static measurement

| | $^{192}OsO_3$ (V) | $^{184}OsO_3$ (μV) | $^{186}OsO_3$ (mV) | $^{187}OsO_3$ (mV) | $^{184}Os/^{188}Os$ | $^{186}Os/^{188}Os$ | $^{187}Os/^{188}Os$ |
|---|---|---|---|---|---|---|---|
| LOsT$^a$ | 0.4-0.5 | 197 | 18 | 16 | 0.001301 ± 3 | 0.119852 ± 12 | 0.106919 ± 15 |
| DROsS$^a$ | 0.2-0.3 | 112 | 10 | 9 | | 0.119851 ± 22 | 0.106924 ± 23 |
| | 0.1-0.2 | 48 | 4 | 4 | | 0.119848 ± 47 | 0.106924 ± 34 |
| | 0.04-0.06 | 20 | 2 | 2 | | 0.119865 ± 74 | 0.106913 ± 56 |
| | 0.9-1.0 | 416 | 38 | 51 | 0.001306 ± 3 | 0.119946 ± 8 | 0.160928 ± 10 |
| | 0.4-0.5 | 187 | 18 | 24 | 0.001301 ± 3 | 0.119944 ± 13 | 0.160926 ± 11 |
| | 0.2-0.3 | 112 | 10 | 14 | | 0.119951 ± 18 | 0.160925 ± 14 |
| | 0.1-0.2 | 62 | 5 | 7 | | 0.119953 ± 34 | 0.160928 ± 25 |
| | 0.04-0.06 | 22 | 2 | 3 | | 0.119937 ± 79 | 0.160942 ± 27 |
| WPR-1 | 0.23-0.36 | 131 | 12 | 15 | 0.001300 ± 3 | 0.119869 ± 7 | 0.144558 ± 7 |
| BIR-1a | 0.01-0.03 | 8.8 | 0.7 | 0.8 | 0.001275 ± 46 | 0.120428 ± 42 | 0.133107 ± 499 |
| BHVO-2 | 0.005-0.007 | 4.5 | 0.3 | 0.3 | 0.001324 ± 116 | 0.121315 ± 1859 | 0.146768 ± 1395 |

Note: The signals of $^{184}OsO_3$, $^{186}OsO_3$, and $^{187}OsO_3$ are averages of the corresponding signal range of $^{192}OsO_3$; the error value is expressed to the last decimal place of the ratio.

Table 4 illustrates the Os isotopic data of standard solutions and rock samples by full Os isotope static measurement. Referring to Table 4, according to the embodiment, two groups of single-element Os standard solution DROsS and LOsT determination were designed, both of which were loaded with about 20 ng of total Os, and were measured at $^{192}Os^{16}O_3^-$ signal of approximately 0.05 V, 0.1 V, 0.25 V, 0.5 V, and 0.1 V, respectively.

Table 4 indicates that when the signal of $^{192}Os^{16}O_3^-$ is from 0.04 V to 1.0 V, the corresponding signal of $^{184}Os^{16}O_3^-$ is from about 17 μV to 430μ. The $^{184}Os/^{188}Os$ ratios and precisions of the two groups are consistent, i.e., 0.001306±3 (2 SD, n=10), which are consistent with the results of solution standard LOsT using NTIMS configured with a conventional amplifier ($10^{11}Ω$) at 4 V-8 V of $^{192}Os^{16}O_3^-$ ion beam intensities (0.001310±16, 2 SD, n=7, Nowell et al., 2008), and consistent with the results of LOsT using MC-ICPMS at an intensity of 20 V and 30 V of $^{192}Os^{16}O_3^-$ ion beam intensities ($^{184}Os/^{188}Os$ ratios are 0.001303±24, 2 SD, n=12 and 0.001302±10, 2 SD, n=11, respectively, Nowell et al. 2008). Although the signals are only 1/10-1/30 of those in the prior art, precision is improved by about 3-8 times.

When the $^{192}Os^{16}O_3^-$ ion beam intensity is within 0.5 V-1.0 V, the long-term repeatability of the $^{186}Os/^{188}Os$ and $^{187}Os/^{188}Os$ ratios of the solution standards is consistent with the results of the $^{192}Os^{16}O_3^-$ signal of 4 V-8 V measured by conventional NTIMS (Chu et al., 2015), as well as with the results of the $^{192}Os^{16}O_3$ signal of 30 V measured by conventional MC-ICPMS (Nowell et al., 2008). The long-term repeatability is 3-7 times better than that measured using NTIMS configured with a $10^{12}Ω$ amplifier at $^{192}Os^{16}O_3^-$ signals of 0.47 V-0.95 V.

As shown in Table 4, a set of rock samples were also designed for determination in the embodiment. The three rock samples selected were metamorphic peridotite WPR-1, basalt BIR-1 and basalt BHVO-2. The experimental pretreatment of the three rock samples has been described in detail before and will not be repeated here.

As shown in Table 4, the results indicate that the $^{184}Os/^{188}Os$ ratios of the three rock specimens are consistent with those of the single-element standard solutions within the error range. The $^{184}OsO_3$ signal intensities of BIR-1 and BHVO-2 are extremely low (<700 cps/11 μV), leading to the poor precision of $^{184}Os/^{188}Os$ ratios. Such low signal intensities, which are below the detection limit of any amplifier, can only be detected by ion counters.

The Os isotope ratios of the WPR-1 obtains the same values and better precision when the $^{192}OsO_3$ intensity was 1/10th of that of the conventional method by NTIMS (e.g., Chu et al., 2015a) and the sample size is less than ½ of it. Values and precision of $^{187}Os/^{188}Os$ ratios for the BIR-1a and BHVO-2 samples are consistent with those obtained by previous method using NTIMS with a $10^{13}Ω$ amplifier, but the present invention also provides $^{184}Os/^{188}Os$ and $^{186}Os/^{188}Os$ ratio data, which is impossible with previous static measurement methods.

It is to be understood that the above embodiment is merely exemplary for illustrating the principles of the present, and not intended to be limiting. For a person of ordinary skill in the art, without departing from the spirit and substance of the present invention, various modifications and improvements may be made. Therefore, this invention includes all modifications encompassed within the spirit and scope of the following claims.

What is claimed is:

1. A method for full Os isotope static measurement at a low-content/small-size sample, comprising steps of:

selecting and weighing a rock sample, and dissolving the rock sample with reverse aqua regia to obtain a dissolution liquid;

chemically separating the Os from the dissolution liquid to obtain a purified Os solution, concentrating the purified Os solution to 1 µl in HBr medium;

loading the purified Os solution onto a Pt filament to be determined;

selecting a plurality of Faraday cups and a plurality of ion counters, as well as different types of amplifiers in Thermal Ionization Mass Spectrometry based on different natural abundances of Os isotopes, thereby establishing a cup configuration for the full Os isotope static measurement, wherein each Faraday cup is connected to a corresponding different type of amplifier; wherein:

the plurality of the Faraday cups comprises a center cup (C) fixed to a multicollector housing of the Thermal Ionization Mass Spectrometry, a first low cup (L1), a second low cup (L2), a third low cup (L3), a fourth low cup (L4), a fifth low cup (L5), a first high cup (H1), a second high cup (H2), a third high cup (H3), and a fourth high cup (H4) disposed sequentially outwardly from the center cup; the plurality of the ion counters comprises a first ion counter (IC 1) bound to the center cup, a second ion counter (IC 2) and a third ion counter (IC 3) and a fourth ion counter (IC4) bound in turn to the fifth low cup (L5), and a fifth ion counter (IC5) and a sixth ion counter (IC6) bound in turn to the fourth low cup (L4);

the cup configuration for the full Os isotope static measurement comprises:

$^{188}OsO_3^-$, $^{189}OsO_3^-$, $^{190}OsO_3^-$ and $^{192}Os^{16}O_3^-$ are collected by the second low cup (L2), the first low cup (L1), the center cup (C) and the first high cup (H1) connected to four $10^{12}\Omega$ amplifiers, respectively;

$^{186}OsO_3^-$ and $^{187}OsO_3^-$ are collected by the fourth low cup (L4) and the third low cup (L3) connected to two $10^{13}\Omega$ amplifiers, respectively;

$^{184}OsO_3^-$ is collected by the sixth ion counter (IC6);

$^{195}PtO_3^-$ is collected by the fourth high cup (H4) connected to a $10^{13}\Omega$ amplifier;

$^{198}PtO_2^-$ is collected by the fifth ion counter (IC4);

a heavy oxygen ion beam $^{192}Os^{16}O_2^{17}O^-$ is collected by the second high cup (H2) connected to a $10^{13}\Omega$ amplifier; and a heavy oxygen ion beam $^{192}Os^{16}O_2^{18}O^-$ is collected by the third high cup (H3) connected to a $10^{13}\Omega$ amplifier;

establishing a yield calibration method for ion counters and calibrating yield of the ion counters according to the yield calibration method; wherein the yield calibration method comprises a specific step of:

determining the $^{192}Os^{16}O_3^-$ using the center cup (C) and the ion counters (ICs) by peak-hopping, respectively, wherein the center cup (C) is used to determine the $^{192}Os^{16}O_3^-$ both before and after determining the $^{192}Os^{16}O_3^-$ by the ion counters (ICs);

a yield $Y_N$ of the ion counters (ICs) is expressed as:

$Y_N=(A+D)/2/B\times100\%$;

wherein A is a signal of a first $^{192}Os^{16}O_3^-$ determination using the center cup (C), B is a signal of a $^{192}Os^{16}O_3^-$ determination using the ion counters (ICs), and D is a signal of a second $^{192}Os^{16}O_3^-$ determination using the center cup (C);

performing full Os isotope determination to the sample based on yield calibration of the ion counters by the Thermal Ionization Mass Spectrometry; and processing determined full Os isotope data, so as to obtain a final composition of full Os isotopes.

2. The method, as recited in claim 1, wherein the fifth ion counter (IC5) and the sixth ion counter (IC6) are both compact discrete dynode ion counters (CDD).

3. The method, as recited in claim 1, wherein selecting and weighing the rock sample, and dissolving the rock sample to obtain the dissolution liquid comprises specific steps of:

selecting at least 3 rock samples to be determined and weighing 0.5-1.0 g of each rock sample; and putting the rock samples into a Carius tube (a glass tube), adding 1 ml-3 ml of concentrated HCl and 5 ml-10 ml of concentrated $HNO_3$ to the glass tube, wherein a ratio of $HCl:HNO_3$ is 1:3, sealing the Carius tube, and dissolving the rock samples in an oven at 200° C.-250° C. for 48 hrs-72 hrs, so as to obtain the dissolution liquid.

4. The method, as recited in claim 1, wherein chemically separating the Os from the dissolution liquid to obtain the purified Os solution comprises specific steps of:

distilling the dissolution liquid for extracting the Os; and purifying extracted Os by micro-distillation to obtain a further purified Os solution.

5. The method, as recited in claim 2, wherein chemically separating the Os from the dissolution liquid to obtain the purified Os solution comprises specific steps of:

distilling the dissolution liquid for extracting the Os; and purifying extracted Os by micro-distillation to obtain a further purified Os solution.

6. The method, as recited in claim 3, wherein chemically separating the Os from the dissolution liquid to obtain the purified Os solution comprises specific steps of:

distilling the dissolution liquid for extracting the Os; and purifying extracted Os by micro-distillation to obtain a further purified Os solution.

7. The method, as recited in claim 1, wherein loading the purified Os solution onto the Pt filament to be determined comprises specific steps of:

concentrating the purified Os solution in HBr medium to 1 µl-2 µl, loading the purified Os solution onto a high-purity Pt filament and drying; loading 1 µl~2 µl of $Ba(OH)_2$ at a concentration of 10 ppm-20 ppm on dried sample as an activator, and drying to obtain the sample to be determined.

8. The method, as recited in claim 2, wherein loading the purified Os solution onto the Pt filament to be determined comprises specific steps of:

concentrating the purified Os solution in HBr medium to 1 µl-2 µl, loading the purified Os solution onto a high-purity Pt filament and drying; loading 1 µl~2 µl of $Ba(OH)_2$ at a concentration of 10 ppm-20 ppm on dried sample as an activator, and drying to obtain the sample to be determined.

9. The method, as recited in claim 3, wherein loading the purified Os solution onto the Pt filament to be determined comprises specific steps of:

concentrating the purified Os solution in HBr medium to 1 µl-2 µl, loading the purified Os solution onto a high-purity Pt filament and drying; loading 1 µl~2 µl of $Ba(OH)_2$ at a concentration of 10 ppm-20 ppm on dried sample as an activator, and drying to obtain the sample to be determined.

10. The method, as recited in claim 1, wherein performing full Os isotope determination to the sample based on the yield calibration of the ion counters by the Thermal Ionization Mass Spectrometry comprises specific steps of:

during measurement, maintaining an oxygen pressure at $1.5\times10^{-7}$ mbar-$2.5\times10^{-7}$ mbar and analyzing for 1 hr-1.5 hr per each time, wherein an evaporation filament temperature is 700° C.-830° C. for Os single-element solution standard measurement, and an evaporation filament temperature is 830° C.-890° C. for rock sample measurement; and before and after each sample measurement, determining $^{185}\text{ReO}_3$ and $^{183}\text{WO}_3$ using an SEM (secondary electron multiplier) by peak-hopping method to monitor isobaric interferences of Re and W;

wherein a peak-hopping analytical parameter ranges from 5 cycles×1 block to 15 cycles×1 block, an integration time ranges from 2 s-5 s, and a time period of one measurement ranges from 1 min-2 min.

11. The method, as recited in claim 2, wherein performing full Os isotope determination to the sample based on the yield calibration of the ion counters by the Thermal Ionization Mass Spectrometry comprises specific steps of:

during measurement, maintaining an oxygen pressure at $1.5 \times 10^{-7}$ mbar-$2.5 \times 10^{-7}$ mbar and analyzing for 1 hr-1.5 hr per each time, wherein an evaporation filament temperature is 700° C.-830° C. for Os single-element solution standard measurement, and an evaporation filament temperature is 830° C.-890° C. for rock sample measurement; and before and after each sample measurement, determining $^{185}\text{ReO}_3$ and $^{183}\text{WO}_3$ using an SEM (secondary electron multiplier) by peak-hopping method to monitor isobaric interferences of Re and W;

wherein a peak-hopping analytical parameter ranges from 5 cycles×1 block to 15 cycles×1 block, an integration time ranges from 2 s-5 s, and a time period of one measurement ranges from 1 min-2 min.

12. The method, as recited in claim 3, wherein performing full Os isotope determination to the sample based on the yield calibration of the ion counters by the Thermal Ionization Mass Spectrometry comprises specific steps of:

during measurement, maintaining an oxygen pressure at $1.5 \times 10^{-7}$ mbar-$2.5 \times 10^{-7}$ mbar and analyzing for 1 hr-1.5 hr per each time, wherein an evaporation filament temperature is 700° C.-830° C. for Os single-element solution standard measurement, and an evaporation filament temperature is 830° C.-890° C. for rock sample measurement; and before and after each sample measurement, determining $^{185}\text{ReO}_3$ and $^{183}\text{WO}_3$ using an SEM (secondary electron multiplier) by peak-hopping method to monitor isobaric interferences of Re and W;

wherein a peak-hopping analytical parameter ranges from 5 cycles×1 block to 15 cycles×1 block, an integration time ranges from 2 s-5 s, and a time period of one measurement ranges from 1 min-2 min.

13. The method, as recited in claim 1, wherein processing the determined full Os isotope data, so as to obtain the final composition of the full Os isotopes comprises a specific step of:

exporting the data for offline correction processing; wherein the offline correction processing comprises removing the isobaric interferences of $\text{PtO}_2$, $\text{PtO}_3$, $\text{ReO}_3$ and $\text{WO}_3$, subtracting interferences of heavy O isotopes in oxides, and performing an instrumental mass fractionation correction by a logarithmic law using $^{192}\text{Os}/^{188}\text{Os}=3.083$.

14. The method, as recited in claim 2, wherein processing the determined full Os isotope data, so as to obtain the final composition of the full Os isotopes comprises a specific step of:

exporting the data for offline correction processing; wherein the offline correction processing comprises removing the isobaric interferences of $\text{PtO}_2$, $\text{PtO}_3$, $\text{ReO}_3$ and $\text{WO}_3$, subtracting interferences of heavy O isotopes in oxides, and performing an instrumental mass fractionation correction by a logarithmic law using $^{192}\text{Os}/^{188}\text{Os}=3.083$.

15. The method, as recited in claim 3, wherein processing the determined full Os isotope data, so as to obtain the final composition of the full Os isotopes comprises a specific step of:

exporting the data for offline correction processing; wherein the offline correction processing comprises removing the isobaric interferences of $\text{PtO}_2$, $\text{PtO}_3$, $\text{ReO}_3$ and $\text{WO}_3$, subtracting interferences of heavy O isotopes in oxides, and performing an instrumental mass fractionation correction by a logarithmic law using $^{192}\text{Os}/^{188}\text{Os}=3.083$.

16. The method, as recited in claim 1, wherein before performing full Os isotope determination to the sample based on the yield calibration of the ion counters by the Thermal Ionization Mass Spectrometry, the method further comprises a step of:

automatically calibrating an amplifier gain according to an automatic calibration method by the Thermal Ionization Mass Spectrometry.

17. The method, as recited in claim 2, wherein before performing full Os isotope determination to the sample based on the yield calibration of the ion counters by the Thermal Ionization Mass Spectrometry, the method further comprises a step of:

automatically calibrating an amplifier gain according to an automatic calibration method by the Thermal Ionization Mass Spectrometry.

18. The method, as recited in claim 3, wherein before performing full Os isotope determination to the sample based on the yield calibration of the ion counters by the Thermal Ionization Mass Spectrometry, the method further comprises a step of:

automatically calibrating an amplifier gain according to an automatic calibration method by the Thermal Ionization Mass Spectrometry.

* * * * *